US012648950B2

(12) United States Patent
Umrethia et al.

(10) Patent No.: US 12,648,950 B2
(45) Date of Patent: Jun. 9, 2026

(54) ORAL LIQUID FORMULATION OF RIVAROXABAN

(71) Applicant: Liqmeds Worldwide Limited, Weedon (GB)

(72) Inventors: Manish Umrethia, Ahmedabad (IN); Chintan Pansara, Ahmedabad (IN)

(73) Assignee: Liqmeds Worldwide Limited, Weedon (GB)

( * ) Notice: Subject to any disclaimer, the term of this patent is extended or adjusted under 35 U.S.C. 154(b) by 0 days.

(21) Appl. No.: 19/047,053

(22) Filed: Feb. 6, 2025

(65) Prior Publication Data

US 2025/0177411 A1     Jun. 5, 2025

Related U.S. Application Data

(63) Continuation-in-part of application No. PCT/IB2024/057596, filed on Aug. 6, 2024.

(30) Foreign Application Priority Data

Aug. 7, 2023     (IN) .............................. 202321052903

(51) Int. Cl.
*A61K 31/5377*     (2006.01)
*A61K 9/00*     (2006.01)

(52) U.S. Cl.
CPC ........ *A61K 31/5377* (2013.01); *A61K 9/0053* (2013.01)

(58) Field of Classification Search
CPC .......................... A61K 31/5377; A61K 9/0053
See application file for complete search history.

(56) References Cited

U.S. PATENT DOCUMENTS

2021/0267908 A1 *     9/2021 Singh .................... A61K 9/4866
2022/0409626 A1 *     12/2022 Hou ..................... A61K 9/2095

FOREIGN PATENT DOCUMENTS

| CN | 105796492 | B | 7/2019 |
| CN | 113750044 | A | 12/2021 |
| WO | 2009/156082 | A1 | 12/2009 |
| WO | 2012/080184 | A2 | 6/2012 |
| WO | WO-2015097090 | A1 * | 7/2015 ........... A61K 31/437 |

OTHER PUBLICATIONS

WO 2012/080184 A2 Translation, Jun. 21, 2012 (Year: 2012).*
CN 113750044 A, Translation, Dec. 7, 2021 (Year: 2021).*
Handbook of Pharmaceutical Excipients, 5th edition 2006, pp. 301, 652, gmpua.com/RD/RD/HandbookPharmaceutica%20Excipients. pdf. (Year: 2006).*
PennWhite, Jan. 9, 2023, api.pennwhite.co.uk/pdf/TDS%20Antifoam% 20Silicone%20Emulsion.pdf. (Year: 2023).*
Xarelto®, (rivaroxaban) 2021, janssenlabels.com/package-insert/ product-monograph/prescribing-information/XARELTO-pi.pdf. (Year: 2021).*
Xarelto (Rivaroxaban) Tablet and For Oral Suspension, Prescribing Information, Janssen Pharmaceuticals, Inc., Dec. 2021, 95 pp.

* cited by examiner

*Primary Examiner* — James H Alstrum-Acevedo
*Assistant Examiner* — Manahil Mirghani Ali Abdalhameed
(74) *Attorney, Agent, or Firm* — Merchant & Gould P.C.; Daniel R. Evans; Daniel J. Pereira

(57)     ABSTRACT

Disclosed herein relates to an oral liquid formulation of rivaroxaban. The present invention is specifically related to an oral liquid suspension of rivaroxaban comprising therapeutically effective amount of rivaroxaban, a salt or prodrug thereof; one or more viscosifying agents; one or more buffering agents; at least one wetting agent; at least one vehicle, and one or more pharmaceutically acceptable excipients. Also disclosed herein relates to process of preparation of an oral liquid formulation of rivaroxaban and a method of using the same.

24 Claims, No Drawings

ORAL LIQUID FORMULATION OF RIVAROXABAN

RELATED APPLICATIONS

This application is a continuation-in-part of International Application No. PCT/IB2024/057596, filed on Aug. 6, 2024, which claims priority to Indian Patent Application No. 202321052903, filed on Aug. 7, 2023, the subject matter of which is incorporated by reference.

FIELD

Disclosed herein is an oral liquid formulation of rivaroxaban. Also disclosed herein is a specifically related to an oral liquid formulation of rivaroxaban comprising therapeutically effective amount of rivaroxaban, a salt or prodrug thereof; one or more viscosifying agents; one or more buffering agents; at least one wetting agent; at least one vehicle, and one or more pharmaceutically acceptable excipients. Also disclosed herein related to a process of preparation of an oral liquid formulation of rivaroxaban and a method of using the same.

BACKGROUND

Deep vein thrombosis (DVT) is a blood clot in a vein located deep inside the body of a person usually in a patient's leg. DVT generally occurs when a thrombus (blood clot) develops in veins deep inside someone's body because of the injured veins or the sluggish blood flowing through the veins. Symptoms can include pain, swelling, redness and enlarged veins in the affected area. The most common life-threatening concern with DVT is the potential for a clot to embolize (detach from the veins), travel as an embolus through the right side of the heart, and become lodged in a pulmonary artery that supplies blood to the lungs. This is called a pulmonary embolism (PE). DVT and PE comprise the cardiovascular disease of venous thromboembolism (VTE).

Anticoagulants are a group of medications that decrease your blood's ability to clot. They can break down existing clots or prevent clots from forming in the first place. These medications can help to stop life-threatening conditions like strokes, heart attacks and pulmonary embolisms, all of which can happen because of blood clots. The anticoagulants include low molecular weight heparins (LMWHs), unfractionated heparin (UFH), factor Xa inhibitors: oral (for example: rivaroxaban, apixaban, edoxaban) and parenteral (fondaparinux), direct thrombin inhibitors: oral (dabigatran etexilate) and parenteral (argatroban, bivalirudin, desirudin), and warfarin.

Among the anticoagulant drugs, rivaroxaban is a tasteless, non-hygroscopic, white to yellowish powder, is a low-solubility, high-permeability drug used to prevent the formation of Deep Vein Thrombosis (DVT) and Pulmonary Embolism (PE) in patients after hip and knee replacement. Can also be used for preventing cerebral apoplexy and non-central nervous system embolism of patients with non-valvular atrial fibrillation, and reducing the risk of coronary artery syndrome recurrence.

Rivaroxaban, sold under the brand name Xarelto among others, is an anticoagulant medication (blood thinner) used to treat and prevent blood clots. Specifically, it is used to treat deep vein thrombosis and pulmonary emboli and prevent blood clots in atrial fibrillation and following hip or knee surgery. It is generally administered orally.

Rivaroxaban competitively inhibits free and clot bound factor Xa. Factor Xa is needed to activate prothrombin (factor II) to thrombin (factor IIa). Thrombin is a serine protease that is required to activate fibrinogen to fibrin, which is the loose meshwork that completes the clotting process. Since one molecule of factor Xa can generate more than 1000 molecules of thrombin, selective inhibitors of factor Xa are profoundly useful in terminating the amplification of thrombin generation. The action of rivaroxaban is irreversible.

In pharmacology, bioavailability is a subcategory of absorption and is the fraction (%) of an administered drug that reaches the systemic circulation. Sometimes drug absorption is measured in terms of bioavailability. Bioavailability is the ability of a drug or other substance to be absorbed and used by the body. The rate of the drug absorbed determines the onset of action of the drug. The various formulations of the drugs take different time for getting absorbed and showing their effect on the site of action. Tablet and capsule formulation are the most used formulation, but the tablets and capsule take time for absorption as first they need to be dissolved and disintegrate before absorption. To overcome the disadvantages of tablets and capsules, oral liquid formulations of different drugs have been developed. Liquid formulations of drugs have faster absorption rate and ultimately have a higher bioavailability. Also, liquid formulations are in better compliance with children and patients of various age groups as they are easy to administer.

Currently, the marketed formulation of rivaroxaban is in the form of tablets. Also, most of the suspensions available in the market are for the reconstitution of rivaroxaban into a suspension, but there are certain disadvantages of reconstitution. Inappropriately reconstituted medications, can lead to adverse effects, including both under doses and overdoses of drugs leading treatment failures. Moreover, reconstituting of drugs cannot be done by a common man thus leading to help from a technically advanced person. Thus, reconstituting of drugs sometimes require technical assistance. Hence, there is need to develop an oral liquid formulation of rivaroxaban which will overcome the above stated disadvantages of the above dosage forms and will also provide faster onset of action in life-threatening disease.

Therefore, the inventors of the present formulation disclosed herein have developed an oral liquid formulation of rivaroxaban with aims to overcome problems cited above by preparing an oral liquid formulation of rivaroxaban.

OBJECTIVES

The main objective disclosed herein relates to an oral liquid formulation of rivaroxaban.

Another objective provides an oral liquid formulation of rivaroxaban which is stable.

Yet another objective provides an oral liquid formulation of rivaroxaban which provides better patient compliance.

Yet another objective provides an oral liquid formulation of rivaroxaban which permits large scale manufacture.

Yet another objective provides an oral liquid formulation of rivaroxaban which gives faster absorption and quicker onset of action.

SUMMARY

The formulation disclosed herein relates to an oral liquid formulation of rivaroxaban.

The main aspect disclosed herein provides an oral liquid formulation of rivaroxaban.

The main aspect of disclosed herein provides an oral liquid formulation of rivaroxaban comprising a therapeutically effective amount of rivaroxaban, a salt or prodrug thereof; one or more viscosifying agents; one or more buffering agents; at least one wetting agent; at least one vehicle, and one or more pharmaceutically acceptable excipients.

Another aspect disclosed herein provides an oral liquid formulation of rivaroxaban consisting of a therapeutically effective amount of rivaroxaban, a salt or prodrug thereof; one or more viscosifying agents; one or more buffering agents; at least one wetting agent; at least one vehicle, and one or more pharmaceutically acceptable excipients.

Another aspect disclosed herein provides an oral liquid formulation comprising a therapeutically effective amount of rivaroxaban, a salt or prodrug thereof; one or more viscosifying agents; one or more buffering agents; at least one wetting agent; at least one vehicle, and one or more pharmaceutically acceptable excipients.

Another aspect disclosed herein provides an oral liquid formulation consisting of a therapeutically effective amount of rivaroxaban, a salt or prodrug thereof; one or more viscosifying agents; one or more buffering agents; at least one wetting agent; at least one vehicle, and one or more pharmaceutically acceptable excipients.

Another aspect disclosed herein provides a process for the preparation of an oral liquid formulation comprising rivaroxaban, a salt or prodrug thereof.

One more aspect disclosed herein is to provide an oral liquid formulation of rivaroxaban comprising a therapeutically effective amount of rivaroxaban, a salt or prodrug thereof used for the treatment to inhibiting platelet aggregation induced by thrombin and preventing blood clots formation, reduction of risk of stroke and systemic embolism in nonvalvular atrial fibrillation, treatment of deep vein thrombosis, treatment of pulmonary embolism, reduction in the risk of recurrence of deep vein thrombosis and/or pulmonary embolism, prophylaxis of deep vein thrombosis following hip or knee replacement surgery, prophylaxis of venous thromboembolism in acutely ill medical patients at risk for thromboembolic complications not at high risk of bleeding, reduction of risk of major cardiovascular events in patients with coronary artery disease (CAD), reduction of risk of major thrombotic vascular events in patients with peripheral artery disease (PAD), including patients after lower extremity revascularization due to symptomatic PAD, treatment of venous thromboembolism and reduction in risk of recurrent venous thromboembolism in pediatric patients, thromboprophylaxis in pediatric patients with congenital heart disease after the fontan procedure.

One more aspect disclosed herein provides an oral liquid formulation comprising a therapeutically effective amount of rivaroxaban, a salt or prodrug thereof for use as a medicament for the treatment to inhibiting platelet aggregation induced by thrombin and preventing blood clots formation, reduction of risk of stroke and systemic embolism in nonvalvular atrial fibrillation, treatment of deep vein thrombosis, treatment of pulmonary embolism, reduction in the risk of recurrence of deep vein thrombosis and/or pulmonary embolism, prophylaxis of deep vein thrombosis following hip or knee replacement surgery, prophylaxis of venous thromboembolism in acutely ill medical patients at risk for thromboembolic complications not at high risk of bleeding, reduction of risk of major cardiovascular events in patients with coronary artery disease (CAD), reduction of risk of major thrombotic vascular events in patients with peripheral artery disease (PAD), including patients after lower extremity revascularization due to symptomatic PAD, treatment of venous thromboembolism and reduction in risk of recurrent venous thromboembolism in pediatric patients, thromboprophylaxis in pediatric patients with congenital heart disease after the fontan procedure.

One or more aspect disclosed herein provides rivaroxaban may be used alone or in combination with other anticoagulant agents.

DETAILED DESCRIPTION

The main embodiment disclosed herein related to an oral liquid formulation of rivaroxaban.

The detailed description set forth below is intended as a description of exemplary embodiments and is not intended to represent the only forms in which the exemplary embodiments may be constructed and/or utilized. The description sets forth the functions and the sequence of steps for constructing and/or operating the exemplary embodiments. However, it is to be understood that the same or equivalent functions and sequences which may be accomplished by different exemplary methods are also intended to be encompassed within the spirit and scope of the invention.

As defined herein, all scientific and technical terms used herein have the same meaning as commonly understood by one of ordinary skill with respect to pharmaceutical sciences.

Although any process and materials similar or equivalent to those described herein can be used in the practice or testing formulation disclosed herein, the specific methods and materials are now described.

The singular forms "a," "an" and "the" specifically also encompass the plural forms of the terms to which they refer, unless the content clearly dictates otherwise. The expressions "about" is used herein to means approximately, in the region of, roughly, or around.

As stated herein, the expressions "comprise(s)" and "comprising" have their customary meanings. When used in the context of a process, the term "comprising" means that the process includes at least the recited steps, but may include additional steps. When used in the context of a composition, the expressions "comprising" means that the composition includes at least the recited features or components, but may also include additional features or components. One will understand that the expression "consisting of" may replace the expression "comprising" for a claimed formulation, process, or method. One will further understand that the expression "consisting essentially of" may replace the expression "comprising" for a claimed formulation, process or method.

The following expressions are used interchangeably herein: "active", "drug", and "active ingredient".

A "therapeutically effective amount" or "effective amount" is that amount of a pharmaceutical agent to achieve a pharmacological effect. The expressions "therapeutically effective amount" includes, for example, a prophylactically effective amount.

As used herein the expressions "liquid formulation" refers to liquid oral formulation like solution, suspension or emulsion, more specifically in the form of suspension.

The expression "about" is used synonymously with the expression "approximately." As one of ordinary skill would understand, the exact boundary of "about" will depend on the component of the composition. Illustratively, the use of the term "about" indicates that values slightly outside the cited values, i.e., plus or minus 0.1% to 10%, which are also effective and safe. Thus, compositions slightly outside the cited ranges are also encompassed by the scope of the present claims.

By the expressions "pH", as used herein, is meant "apparent pH" wherein the pH measurement is carried out on the rivaroxaban containing composition in final form, for example, by measuring the pH of the formulation.

The main embodiment disclosed herein provides an oral liquid formulation of rivaroxaban comprising a therapeutically effective amount of rivaroxaban, a salt or prodrug thereof; one or more viscosifying agents; one or more buffering agents; at least one wetting agent; at least one vehicle, and one or more pharmaceutically acceptable excipients.

The aspect disclosed herein provides an oral liquid formulation of rivaroxaban consisting of a therapeutically effective amount of rivaroxaban, a salt or prodrug thereof; one or more viscosifying agents; one or more buffering agents; at least one wetting agent; at least one vehicle, and one or more pharmaceutically acceptable excipients.

As per one embodiment disclosed herein provides an oral liquid formulation comprising a therapeutically effective amount of rivaroxaban, a salt or prodrug thereof; one or more viscosifying agents; one or more buffering agents; at least one wetting agent; at least one vehicle, and one or more pharmaceutically acceptable excipients.

As per one embodiment disclosed herein provides an oral liquid formulation consisting of a therapeutically effective amount of rivaroxaban, a salt or prodrug thereof; one or more viscosifying agents; one or more buffering agents; at least one wetting agent; at least one vehicle, and one or more pharmaceutically acceptable excipients.

As per one embodiment disclosed herein, rivaroxaban can be present in the formulation in an amount of from about 0.5 mg/mL to 500 mg/mL, and all values in between, such as, from about 1 mg/mL to about 200 mg/mL, from about 1 mg/mL to about 150 mg/mL, from about 1 mg/mL to about 100 mg/mL, from about 1 mg/mL to about 50 mg/mL, from about 1 mg/mL to about 40 mg/mL, from about 1 mg/mL to about 30 mg/mL, from about 1 mg/mL to about 10 mg/mL, about 1 mg/mL, or 1 mg/mL, about 2 mg/mL, or 2 mg/mL, about 4 mg/mL or 4 mg/mL.

The formulation disclosed herein comprises particulate rivaroxaban having a particle size distribution between about 5 microns to about 30 microns (D10), between about 40 microns to about 80 microns (D50), and between about 100 microns to about 150 microns (D90), and all values in between, such as 104 microns, 108 microns, 112 microns, 116 microns, 120 microns, 124 microns, 128 microns, 132 microns, 136 microns, 140 microns, 144 microns, and 148 microns.

In one aspect, rivaroxaban is the only active pharmaceutical ingredient in the formulation.

In another aspect, the formulation disclosed herein has a viscosity after storage at 25±2° C. and 60±5% RH of about 200 cP to about 600 cP, and including all values in between, such as, 205 cP, 210 cP, 215 cP, 220 cP, 225 cP, 230 cP, 235 cP, 240 cP, 245 cP, 250 cP, 260 cP, 270 cP, 280 cP, 290 cP, 300 cP, 320 cP, 340 cP, 360 cP, 380 cP, 400 cP, 420 cP, 440 cP, 460 cP, 480 cP, 500 cP, 520 cP, 540 cP, 560 cP, and 580 cP.

A further aspect relates to an oral liquid formulation comprising therapeutically effective amount of rivaroxaban, a salt or prodrug thereof; one or more viscosifying agents; one or more buffering agents; at least one wetting agent; at least one vehicle, and one or more pharmaceutically acceptable excipients and a means for providing a formulation viscosity of from 200 cP to 600 cP (including all values in between).

Yet a further aspect relates to an oral liquid formulation comprising therapeutically effective amount of rivaroxaban, a salt or prodrug thereof in an amount of about 1 mg/mL to about 10 mg/mL and having a D90 particle size of between about 100 microns to about 150 microns (and all values in between); at least one vehicle, and one or more pharmaceutically acceptable excipients and a means for providing a formulation viscosity of from 200 cP to 600 cP (including all values in between).

Yet another aspect relates to a liquid formulation comprising rivaroxaban in an amount of about 2 mg/mL or about 4 mg/mL; one or more pharmaceutically acceptable excipients; a vehicle comprising glycerin and water and a means for providing a sedimentation volume of not more than 1 mL of clear liquid after the liquid formulation stands after 24-hours at room temperature.

Yet another aspect relates to a liquid formulation comprising rivaroxaban in an amount of about 2 mg/mL or about 4 mg/mL; one or more pharmaceutically acceptable excipients; a vehicle comprising glycerin and water and a means for providing a suitable resuspendability after shaking for at least 30-seconds, where the suitable resuspendability relates to a labelled content of rivaroxaban of either about 2 mg/mL or about 4 mg/mL in the liquid formulation.

As per another embodiment, one or more viscosifying agents can be selected from Avicel-RC 591, a combination of microcrystalline cellulose, and carboxymethylcellulose sodium, microcrystalline cellulose, sodium carboxymethyl cellulose, hydroxypropylmethylcellulose (HPMC), xanthan gum, acacia, and guar gum, or any combination thereof.

As per another embodiment, Avicel-RC 591 or a combination of microcrystalline cellulose, and carboxymethylcellulose sodium are same or interchangeable. One will appreciate that Avicel RC-591 comprises a blend of about 82% to about 89% of microcrystalline cellulose and about 11 to 18% of sodium carboxymethylcellulose.

As per one embodiment, one or more viscosifying agents, alternatively a combination of two viscosifying agents. As per one aspect, the formulation disclosed herein comprises combination of Avicel-RC 591 and xanthan gum as the viscosifying agent.

As per one embodiment, Avicel-RC 591 or one or more viscosifying agents can be used in the range of from about 0.5 mg/mL-about 30 mg/mL, and all values in between, such as, from about 0.5 mg/mL-about 20 mg/mL, from about 1 mg/mL-about 20 mg/mL, and from about 1 mg/mL-about 18 mg/mL, as well as, for example, about 2 mg/mL, about 3.5 mg/mL, about 4 mg/mL, about 6 mg/mL, about 8 mg/mL, about 10 mg/mL, about 12 mg/mL, about 14 mg/mL, about 15.5 mg/mL, about 16 mg/mL, about 18 mg/mL, about 20 mg/mL, about 24 mg/mL, and about 28 mg/mL.

As per one embodiment, xanthan gum or one or more viscosifying agents can be used in the range of from about 0.5 mg/mL-about 30 mg/mL, and all values in between, such as, from about 0.5 mg/mL-about 20 mg/mL, from about 1 mg/mL-about 20 mg/mL, and from about 1 mg/mL-about 18 mg/mL, as well as, for example, about 1 mg/mL, about 2 mg/mL, about 3.5 mg/mL, about 4 mg/mL, about 6 mg/mL, about 8 mg/mL, about 10 mg/mL, about 12 mg/mL, about 14 mg/mL, about 15.5 mg/mL, about 16 mg/mL, about 18 mg/mL, about 20 mg/mL, about 24 mg/mL, and about 28 mg/mL.

A further aspect relates to a liquid formulation comprising rivaroxaban in an amount of about 2 mg/mL or about 4 mg/mL; about 9.8 mg/mL to about 10.7 mg/mL of microcrystalline cellulose, about 1.3 mg/mL to about 2.3 mg/mL of carboxymethylcellulose sodium, and about 3 mg/mL to about 4 mg/mL xanthan gum; a combination of sodium citrate, and citric acid; sodium lauryl sulfate; glycerin in water as a vehicle, and one or more pharmaceutically acceptable excipients.

A further aspect relates to a liquid formulation comprising rivaroxaban in an amount of about 2 mg/mL or about 4 mg/mL; about 9.8 mg/mL to about 10.7 mg/mL of microcrystalline cellulose, about 1.3 mg/mL to about 2.3 mg/mL of carboxymethylcellulose sodium, and about 3.5 mg/mL xanthan gum; a combination of sodium citrate, and citric acid; sodium lauryl sulfate; glycerin in water as a vehicle, and one or more pharmaceutically acceptable excipients.

A further aspect relates to a liquid formulation comprising rivaroxaban in an amount of about 2 mg/mL or about 4 mg/mL; about 9.8 mg/mL to about 10.7 mg/mL of microcrystalline cellulose, about 1.3 mg/mL to about 2.3 mg/mL of carboxymethylcellulose sodium, and about 3 mg/mL to about 4 mg/mL xanthan gum; a combination of sodium citrate, and citric acid; about 1 mg/mL of sodium lauryl sulfate; about 50 mg/mL to about 200 mg/mL glycerin in water as a vehicle, and one or more pharmaceutically acceptable excipients, such as 30% simethicone, a sweetener, a preservative, and a flavorant.

A further aspect relates to a liquid formulation comprising rivaroxaban in an amount of about 2 mg/mL or about 4 mg/mL; about 9.8 mg/mL to about 10.7 mg/mL of microcrystalline cellulose, about 1.3 mg/mL to about 2.3 mg/mL of carboxymethylcellulose sodium, and about 3 mg/mL to about 4 mg/mL xanthan gum; a combination of sodium citrate, and citric acid; about 1 mg/mL of sodium lauryl sulfate; about 50 mg/mL glycerin in water as a vehicle, and one or more pharmaceutically acceptable excipients, such as 30% simethicone, a sweetener, a preservative, and a flavorant.

The buffers used in the formulation disclosed herein are generally recognized as safe (GRAS) by the U.S. Food and Drug Administration.

As per one embodiment, one or more buffering agents can be selected from sodium citrate, sodium acetate trihydrate, phosphate, citric acid, tris, succinate, histidine, glycine, arginine, malic, tartaric, acetic, benzoic, gluconic, glyceric, lactic, adipic, ascorbic, carbonic, glutamic, ammonium chloride, triethanolamine and salts or acids thereof or any combination thereof.

As per one embodiment, the formulation disclosed herein comprises one or more buffering agents, alternatively a combination of two buffering agents. As per one aspect, the formulation disclosed herein comprises combination of sodium citrate and citric acid as the buffering agent.

As per one embodiment, sodium citrate (or one or more buffering agents) can be used in the range of from about 0.5 mg/mL-about 30 mg/mL, and all values in between, such as, from about 0.5 mg/mL-about 20 mg/mL, from about 1 mg/mL-about 20 mg/mL, and from about 1 mg/mL-about 15 mg/mL, as well as, for example, about 1 mg/mL, about 2 mg/mL, about 4 mg/mL, about 5 mg/mL, about 6 mg/mL, about 6.4 mg/mL, about 8 mg/mL, about 10 mg/mL, about 11.4 mg/mL, about 12 mg/mL, about 14 mg/mL, about 16 mg/mL, about 18 mg/mL, about 20 mg/mL, about 24 mg/mL, and about 28 mg/mL.

As per one embodiment, citric acid (or one or more buffering agents) can be used in the range of from about 0.5 mg/mL-about 30 mg/mL, and all values in between, such as, from about 0.5 mg/mL-about 20 mg/mL, from about 1 mg/mL-about 30 mg/mL, from about 1 mg/mL-about 25 mg/mL, and from about 1 mg/mL-20 mg/mL, as well as, for example, about 1 mg/mL, about 2 mg/mL, about 4 mg/mL, about 5 mg/mL, about 6 mg/mL, about 6.4 mg/mL, about 8 mg/mL, about 10 mg/mL, about 11.4 mg/mL, about 12 mg/mL, about 14 mg/mL, about 16 mg/mL, about 18 mg/mL, about 20 mg/mL, about 24 mg/mL, and about 28 mg/mL.

As per one another embodiment, at least one wetting agent can be selected from sodium lauryl sulfate, simethicone, sodium tetradecyl sulfate, dodecyl sulfate, lauryl glucoside or any combination thereof.

As per one aspect, sodium lauryl sulfate is used as surfactant or a wetting agent.

As per one embodiment, sodium lauryl sulfate (or at least one wetting agent) can be used in the range of from about 0.5 mg/mL-about 20 mg/mL and all values in between, such as, from about 1 mg/mL-about 20 mg/mL, and from about 0.5 mg/mL-about 10 mg/mL, as well as, for example, about 1 mg/mL, about 3 mg/mL, about 5 mg/mL, about 7 mg/mL, about 9 mg/mL, about 11 mg/mL, about 13 mg/mL, about 15 mg/mL, about 17 mg/mL, and about 19 mg/mL.

As per one embodiment, the one or more pharmaceutically acceptable excipients can be selected from anti foaming agent, sweetening agent, preservative, and flavouring agent.

As per another embodiment, the expressions "inactive excipients" or "pharmaceutically acceptable excipients" are same or interchangeable.

As per one embodiment, at least one anti-foaming agent can be selected from simethicone, organic phosphates, stearates, alcohols, paraffin oils, and glycols or any combination thereof.

As per one aspect, simethicone is used as anti-foaming agent, such as 30% simethicone emulsion.

As per one embodiment, simethicone (or at least one anti-foaming agent) can be used in the range of from about 0.5 mg/mL about 20 mg/mL, and all values in between, such as, from about 1 mg/mL-about 20 mg/mL, and from about 1 mg/mL-about 10 mg/mL, as well as, for example, about 1 mg/mL, about 3 mg/mL, about 5 mg/mL, about 7 mg/mL, about 9 mg/mL, about 11 mg/mL, about 13 mg/mL, about 15 mg/mL, about 17 mg/mL, and about 19 mg/mL.

As per one embodiment, at least one sweetening agent can be selected from but not limited to sucralose, trehalose, xylose, dextrose, tagatose, glycerol, dulcitol, lactitol, saccharine or the corresponding sodium, potassium or calcium salt, cyclamate or the corresponding sodium or calcium salt, aspartame, or acesulfame or the potassium salt thereof, ammonium glycyrrhizinate, alitame, inulin, isomalt, neohesperidin dihydrochalcone, thaumatin and the like or any combination thereof.

As per one aspect, sucralose is used as sweetening agent.

As per one embodiment, at least one sweetening agent can be used in the range of from about 0.1 mg/mL-about 20 mg/mL, and all values in between, such as, from about 0.1 mg/mL-about 10 mg/mL, from about 0.5 mg/mL-about 10 mg/mL, and from about 0.5 mg/mL-about 5 mg/mL, as well as, for example, about 0.5 mg/mL, about 1 mg/mL, about 2 mg/mL, about 3 mg/mL, about 5 mg/mL, about 7 mg/mL, about 9 mg/mL, about 11 mg/mL, about 13 mg/mL, about 15 mg/mL, about 17 mg/mL, and about 19 mg/mL.

As per one embodiment, at least one preservative can be selected from but not limited to benzoic acid, potassium sorbate, sodium benzoate, chlorobutanol, ethanol, benzalkonium chloride, benzethonium chloride, benzyl alcohol, chlorobutanol, m-cresol, myristyl gamma picolinium chloride, phenol, 2-phenoxyethanol, phenyl mercuric nitrate, phenyl ethyl alcohol, ethylenediaminetetraacetic acid (EDTA) or any combination thereof.

As per one aspect, sodium benzoate is used as preservative.

As per one embodiment, sodium benzoate (or at least one preservative) can be used in the range of from about 0.01 mg/mL-about 10 mg/mL, and all values in between, such as, from about 0.01 mg/mL-about 8 mg/mL, from about 0.05 mg/mL-about 5 mg/mL, and from about 0.05 mg/mL-about 3 mg/mL, as well as, for example, about 0.05 mg/mL, about 0.1 mg/mL, about 0.5 mg/mL, about 1 mg/mL, about 3 mg/mL, about 5 mg/mL, about 7 mg/mL, about 9 mg/mL.

As per one embodiment, at least one flavouring agent can be selected from but not limited to vanilla, citrus oil, including lemon, orange, grape, lime and grapefruit, and fruit essences, including apple, banana, pear, peach, strawberry, raspberry, cherry, plums pineapple, apricot, peppermint, frozen peppermint, tutti frutti flavour and so forth and the like or any combination thereof.

As per one aspect, frozen peppermint flavour is used as flavouring agent.

As per one embodiment, at least one flavouring agent can be used in the range of from about 0.01 mg/mL-about 1 mg/mL, and all values in between, such as, from about 0.05 mg/mL-about 1 mg/mL, from about 0.05 mg/mL-about 0.8 mg/mL, and from about 0.05 mg/mL-about 0.5 mg/mL, as well as, for example, about 0.05 mg/mL, about 0.1 mg/mL, and about 0.5 mg/mL.

Vehicle can be considered as any inert substance, or mixture of substances, added to increase the volume of the liquid composition disclosed herein to make the liquid formulation disclosed herein in a suitable form.

As per one embodiment, at least one vehicle can be selected from purified water, glycerin, phosphate buffer, propylene glycol, polyethylene glycol (PEG), PEG 400, glycerin containing buffers or any combination thereof.

As per preferred embodiment, glycerin (or combination of glycerin and purified water) is used as vehicle.

As per one embodiment, glycerin can be used in the range of from about 1 mg/mL-about 500 mg/mL, and all values in between, such as, from about 1 mg/mL-about 200 mg/mL, from about 1 mg/mL-about 100 mg/mL, and from about 1 mg/mL-about 50 mg/mL as well as, for example, about 5 mg/mL, about 10 mg/mL, about 20 mg/mL, about 30 mg/mL, about 40 mg/mL, about 50 mg/mL, about 60 mg/mL, about 70 mg/mL, about 90 mg/mL, about 100 mg/mL, about 150 mg/mL, about 200 mg/mL, about 250 mg/mL, about 300 mg/mL, about 350 mg/mL, about 400 mg/mL, and about 450 mg/mL.

As per one embodiment, purified water can be used to adjust the final volume of the formulation.

In yet another aspect, the purified water can be used in the range of from about 500 mg/mL to about 1000 mg/mL, and all values in between, such as, 520 mg/mL, 540 mg/mL, 560 mg/mL, 580 mg/mL, 600 mg/mL, 620 mg/mL, 640 mg/mL, 660 mg/mL, 680 mg/mL, 700 mg/mL, 720 mg/mL, 740 mg/mL, 760 mg/mL, 780 mg/mL, 800 mg/mL, 820 mg/mL, 840 mg/mL, 860 mg/mL, 880 mg/mL, 900 mg/mL, 920 mg/mL, 940 mg/mL, 960 mg/mL, and 980 mg/mL.

In one aspect, the oral liquid formulation disclosed herein does not include a preservative (for example, an alkyl ester of p-hydroxybenzoic acid which includes methyl paraben, propyl paraben, ethyl paraben, butyl paraben etc.), a sugar (for example, glucose, mannitol, fructose, sucrose, maltose, maltitol, galactose, sorbitol, xylitol etc.), a stabilizer (for example, poloxamer, hydroxymethyl cellulose, povidone, polysorbate 80 (Tween 80), sorbitan trioleate (Span 85) etc.), a polar organic solvent (for example, dimethyl sulfoxide (DMSO), acetonitrile etc.), a suspending agent (for example, tragacanth gum, sodium alginate, colloidal silica etc.), a flocculant (for example, potassium chloride).

Another main embodiment relates to a process of preparing an oral liquid formulation of rivaroxaban, comprises:

mixing together a therapeutically effective amount of rivaroxaban, a salt or prodrug thereof; one or more viscosifying agents; one or more buffering agents; at least one wetting agent; at least one vehicle, and one or more pharmaceutically acceptable excipients.

The process may further comprise solubilizing citric acid in purified water to act as one of the buffering agent.

The process may further comprise adding the sodium citrate to the solution.

the process may further comprise adding and mixing of sodium benzoate, sucralose, simethicone, Avicel-RC591 to the solution till gets completely solubilized.

The process may further comprise adding and mixing of sodium lauryl sulfate, glycerin in solution till gets completely solubilized.

The process may further comprise adding and mixing of rivaroxaban in solution till gets completely solubilized.

The process may further comprise adding and mixing xanthan gum in remaining quantity of glycerin in separate vessel and mixing till get homogenously dispersed.

The process may further comprise adding and mixing flavoring agent in solution and mixing it till gets completely dispersed.

The process may further comprise adjusting the volume using purified water, mixing and homogenizing the formulation using homogenizer till homogeneous formulation obtained.

The process may further comprise storing the final formulation in a HDPE bottle.

As per another main embodiment, the process for preparing an oral liquid formulation of rivaroxaban comprises:

a) Adding and mixing citric acid in purified water till gets completely solubilized;

b) Adding and mixing sodium citrate in solution of step (a) till gets completely solubilized;

c) Adding and mixing sodium benzoate in solution of step (b) till gets completely solubilized;

d) Adding and mixing sucralose in solution of step (c) till gets completely solubilized;

e) Adding and mixing simethicone in solution of step (d) till gets completely solubilized;

f) Adding and mixing Avicel-RC 591 in solution of step (e) till gets completely solubilized and till achieve desirable viscosity;

g) Adding and mixing sodium lauryl sulfate in solution of step (f) till gets completely solubilized;

h) Adding and mixing glycerin in solution of step (g) till gets completely solubilized;

i) Adding and mixing rivaroxaban in solution of step (h) till gets completely solubilized;

j) Adding xanthan gum in remaining quantity of glycerin in separate vessel and mixing till get homogenously dispersed;

k) Adding solution of step (h) into slurry of step (j) and continuously stirring the solution till get homogenously dispersed;

l) Adding flavoring agent in solution of step (k) and mixing it till gets completely dispersed;

m) Adjusting the volume of step (l) using purified water, mixing and homogenizing the formulation using homogenizer till homogeneous formulation obtained.

n) Storing the final formulation in a HDPE bottle.

As per one embodiment, an oral liquid formulation of rivaroxaban comprising a therapeutic effective amount of rivaroxaban, a salt or prodrug thereof; a combination of Avicel-RC 591, and xanthan gum as viscosifying agent; a combination of sodium citrate, and citric acid as buffering agent; a sodium lauryl sulfate as a wetting agent, and one or more pharmaceutically acceptable excipients.

As per one embodiment, an oral liquid formulation of rivaroxaban consisting of a therapeutic effective amount of rivaroxaban, a salt or prodrug thereof; a combination of Avicel-RC 591, and xanthan gum as viscosifying agent; a combination of sodium citrate, and citric acid as buffering agent; a sodium lauryl sulfate as a wetting agent, and one or more pharmaceutically acceptable excipients.

As per one embodiment, an oral liquid formulation of rivaroxaban comprising from about 0.5 mg/mL-about 500 mg/mL rivaroxaban, a salt or prodrug thereof; a combination of from about 0.5 mg/mL-about 30 mg/mL Avicel-RC 591, and from about 0.5 mg/mL-about 20 mg/mL xanthan gum as viscosifying agent; a combination of from about 0.5 mg/mL-about 30 mg/mL sodium citrate, and from about 0.5 mg/mL-about 30 mg/mL citric acid as buffering agent; from about 0.5 mg/mL-about 20 mg/mL sodium lauryl sulfate as wetting agent, and one or more pharmaceutically acceptable excipients.

As per one embodiment, an oral liquid formulation of rivaroxaban comprising rivaroxaban, a salt or prodrug thereof; a combination of Avicel-RC 591, and xanthan gum as viscosifying agent; a combination of sodium citrate, and a citric acid as buffering agent; a sodium lauryl sulfate as a wetting agent; a simethicone as antifoaming agent; a sucralose as a sweetening agent; a sodium benzoate as a preservative; a frozen peppermint as a flavouring agent, and a glycerin in water as a vehicle.

As per one embodiment, an oral liquid formulation of rivaroxaban consisting of rivaroxaban, a salt or prodrug thereof; a combination of Avicel-RC 591, and xanthan gum as viscosifying agent; a combination of sodium citrate, and a citric acid as buffering agent; a sodium lauryl sulfate as a wetting agent; a simethicone as antifoaming agent; a sucralose as a sweetening agent; a sodium benzoate as a preservative; a frozen peppermint as a flavouring agent, and a glycerin in water as a vehicle.

As per one embodiment, an oral liquid formulation of rivaroxaban comprising from about 1 mg/mL-about 10 mg/mL rivaroxaban, a salt or prodrug thereof; a combination of from about 1 mg/mL-about 15 mg/mL Avicel-RC 591, and from about 1 mg/mL-about 10 mg/mL xanthan gum as viscosifying agent; a combination of from about 1 mg/mL-about 15 mg/mL sodium citrate, and from about 1 mg/mL-about 20 mg/mL citric acid as buffering agent; from about 0.5 mg/mL-about 10 mg/mL sodium lauryl sulfate as wetting agent; from about 1 mg/mL-about 10 mg/mL simethicone as antifoaming agent; from about 0.5 mg/mL-about 5 mg/mL sucralose as sweetening agent; from about 0.05 mg/mL-about 3 mg/mL sodium benzoate as preservative; from about 0.05 mg/mL-about 0.5 mg/mL frozen peppermint as flavoring agent; from about 1 mg/mL-about 50 mg/mL of glycerin in water as vehicle.

As per one embodiment, an oral liquid formulation of rivaroxaban has a pH range from about 3.5 to about 4.5.

As per one embodiment, the liquid formulation can be selected from solution, suspension or emulsion. In one aspect, the liquid formulation is in the form of a suspension.

In one aspect, the liquid formulation disclosed herein is ready to use (RTU) suspension i.e. ready to be administered directly to a patient for a treatment, without an additional step, such as reconstitution or dilution.

As per one embodiment, the liquid formulation is having at least 90% purity and impurity is less than 5% during the shelf life of, for example, 2-years.

As per one embodiment, an oral liquid formulation of rivaroxaban which is stable and provides better patient compliance.

As per one embodiment, an oral liquid formulation of rivaroxaban comprising rivaroxaban, a salt or prodrug thereof can be useful in inhibiting platelet aggregation induced by thrombin and prevention of blood clots, reduction of risk of stroke and systemic embolism in nonvalvular atrial fibrillation, treatment of deep vein thrombosis, treatment of pulmonary embolism, reduction in the risk of recurrence of deep vein thrombosis and/or pulmonary embolism, prophylaxis of deep vein thrombosis following hip or knee replacement surgery, prophylaxis of venous thromboembolism in acutely ill medical patients at risk for thromboembolic complications not at high risk of bleeding, reduction of risk of major cardiovascular events in patients with coronary artery disease (CAD), reduction of risk of major thrombotic vascular events in patients with peripheral artery disease (PAD), including patients after lower extremity revascularization due to symptomatic PAD, treatment of venous thromboembolism and reduction in risk of recurrent venous thromboembolism in pediatric patients, thromboprophylaxis in pediatric patients with congenital heart disease after the fontan procedure. Therapeutic effective amounts of rivaroxaban may be determined by consulting the XARELTO® (NDA 215859) Prescribing Information, as of Dec. 21, 2021, the subject matter of which is incorporated by reference.

As per one embodiment, an oral liquid formulation comprising rivaroxaban, a salt or prodrug thereof for use as a medicament for the treatment to inhibiting platelet aggregation induced by thrombin and prevention of blood clots, reduction of risk of stroke and systemic embolism in nonvalvular atrial fibrillation, treatment of deep vein thrombosis, treatment of pulmonary embolism, reduction in the risk of recurrence of deep vein thrombosis and/or pulmonary embolism, prophylaxis of deep vein thrombosis following hip or knee replacement surgery, prophylaxis of venous thromboembolism in acutely ill medical patients at risk for thromboembolic complications not at high risk of bleeding, reduction of risk of major cardiovascular events in patients with coronary artery disease (CAD), reduction of risk of major thrombotic vascular events in patients with peripheral artery disease (PAD), including patients after lower extremity revascularization due to symptomatic PAD, treatment of venous thromboembolism and reduction in risk of recurrent venous thromboembolism in pediatric patients, thromboprophylaxis in pediatric patients with congenital heart disease after the fontan procedure.

In one or more aspect. rivaroxaban may be used alone or in combination with other anticoagulant agents.

The formulation disclosed herein is further illustrated by the following examples which are provided to be exemplary of the invention and do not limit the scope of the subject matter claimed herein. While the formulation disclosed herein has been described in terms of its specific embodiments, certain modifications and equivalents will be apparent to those skilled in the art and are intended to be included within the scope of the formulation claimed herein.

EXAMPLES

Example 1: Vehicle Screening

For the selection of vehicle rivaroxaban was dissolved in different vehicles like glycerin alone or in combination with purified water and citrate and phosphate buffer. The stress study was conducted for those batches by 7 days exposure at 60° C.

TABLE 1

Batches for selection of vehicle

| Batch No. | Glycerin | Propylene glycol | PEG-400 | Purified water | 100 mM Citrate buffer pH 4 | 100 mM Phosphate buffer pH 7 |
|---|---|---|---|---|---|---|
| RIRL/120721/1001A | — | — | — | Q.S. to 1 mL | — | — |
| RIRL/120721/1001B | 504 mg/mL | — | — | Q.S. to 1 mL | — | — |
| RIRL/120721/1001C | — | 416 mg/mL | — | Q.S. to 1 mL | — | — |
| RIRL/120721/1001D | — | — | 452 mg/mL | Q.S. to 1 mL | — | — |
| RIRL/120721/1002A | — | — | — | — | Q.S. to 1 mL | — |
| RIRL/120721/1002B | 504 mg/mL | — | — | — | Q.S. to 1 mL | — |
| RIRL/120721/1002C | — | 416 mg/mL | — | — | Q.S. to 1 mL | — |
| RIRL/120721/1002D | — | — | 452 mg/mL | — | Q.S. to 1 mL | — |
| RIRL/120721/1003A | — | — | — | — | — | Q.S. to 1 mL |
| RIRL/120721/1003B | 504 mg/mL | — | — | — | — | Q.S. to 1 mL |
| RIRL/120721/1003C | — | 416 mg/mL | — | — | — | Q.S. to 1 mL |
| RIRL/120721/1003D | — | — | 452 mg/mL | — | — | Q.S. to 1 mL |

Q.S.: Quantity Sufficient.

TABLE 2

Result of stress study of batches for selection of vehicle

| | | Related substance | |
|---|---|---|---|
| Batch No. | pH | Single Max unknown impurity | Total impurities |
| RIRL/120721/1001A | 5.42 | ND | ND |
| RIRL/120721/1001B | 3.98 | 0.02% | 0.03% |
| RIRL/120721/1001C | 4.95 | 0.03% | 0.06% |
| RIRL/120721/1001D | 4.44 | 0.12% | 0.54% |
| RIRL/120721/1002A | 3.9 | 0.03% | 0.12% |
| RIRL/120721/1002B | 4.17 | 0.02% | 0.07% |
| RIRL/120721/1002C | 4.43 | 0.05% | 0.11% |
| RIRL/120721/1002D | 4.79 | 0.01% | 0.05% |
| RIRL/120721/1003A | 7.09 | 0.32% | 0.44% |
| RIRL/120721/1003B | 7.02 | 0.68% | 1.24% |
| RIRL/120721/1003C | 7.7 | 0.52% | 0.64% |
| RIRL/120721/1003D | 7.93 | 1.56% | 3.32% |

Single max unknown impurity: Any single unknown impurity; ND: Not Detected.

Based on above data it was concluded that, in presence of 100 mM phosphate buffer is not compatible with rivaroxaban (1003A, B, C and D batches). Polyethylene glycol (PEG) 400 is not compatible with rivaroxaban in presence of water (001D batch). Propylene glycol (PG) and glycerin are compatible with purified water and 100 mM citrate buffer. To avoid any pH fluctuation during stability and glycerin is being used widely in liquid oral products, further trials were optimized using citrate buffer in combination with glycerin.

Example 2: pH Effect on Development of an Oral Liquid Formulation of Rivaroxaban

TABLE 3

Batches to check the effect of pH

| | Batch no. | | |
|---|---|---|---|
| Ingredients | RIRL/040822/1024 mg/mL | RIRL/050822/1027 mg/mL | RIRL/080822/1030 mg/mL |
| Rivaroxaban | 1 | 1 | 1 |
| Avicel RC 591 | 12 | 12 | 12 |
| Sucralose | 2 | 2 | 2 |
| Xanthan Gum | 3.5 | 3.5 | 3.5 |
| Sodium Benzoate | 1 | 1 | — |
| Methyl paraben/Ethyl paraben | — | — | 1.8/0.2 |
| Citric Acid anhydrous | 6.4 | 2 | — |
| Sodium Citrate | 5 | — | — |
| Disodium phosphate | — | 4.4 | 1 |
| Sodium dihydrogen phosphate | — | — | 2.25 |
| Simethicone | 3 | 3 | 3 |
| SLS | 1 | 1 | 1 |
| Frozen peppermint | 0.1 | 0.1 | 0.1 |
| Glycerin | 100 | 100 | 100 |
| Purified Water | Q.S. to 1 mL | Q.S. to 1 mL | Q.S. to 1 mL |

Q.S.: Quantity Sufficient.

TABLE 4

| Result of stability study to evaluate the effect of pH | | | |
|---|---|---|---|
| | Batch no. | | |
| | RIRL/040822/1024 | RIRL/050822/1027 | RIRL/080822/1030 |
| | | Storage condition | |
| | | 40° C. ± 2° C./NMT 25% RH | |
| | | Time point | |
| | 3 M | 3 M | 3 M |
| Test | | TRF No | |
| parameters | | | |
| | RIRLTRF50066 | RIRLTRF50073 | RIRLTRF50076 |
| Description | White to off white suspension | Off White Suspension | Off White Suspension | Off White Suspension |
| pH | Between 3.5 to 4.5 | 3.79 | 5.51 | 6.25 |
| Assay of API | 90.0-110.0% of labelled amount | 101.4 | 102.2 | 100.5 |
| Single maximum unknown impurity | NMT 0.2% | BQL | ND | 0.7% |
| Total impurities | NMT 0.5% | 0.0% | 0.0% | 0.7% |

NMT: Not More Than;
M: Months;
RH: Relative Humidity;
BQL: Below Quantitation Limit;
TRF No: Test Request Form No.

Based on above data it can be concluded that, batch no. RIRL/080822/1030 (pH 6.25) showed increase level of impurities as compared to batches prepared with pH 3.8 and 5.5. As there is also presence of disodium phosphate in RIRL/050822/1027 and possibility of increase in impurity at longer duration of time, it is concluded to move forward with citrate buffer-based composition (RIRL/040822/1024) for further evaluation for stability studies.

Example 3: Optimized Final Formulation of Oral Liquid Suspension of Rivaroxaban

TABLE 5

| Optimized final formulation of oral liquid suspension of Rivaroxaban | | | |
|---|---|---|---|
| | Quantity (mg/mL) | | |
| | Batch No. | | |
| Ingredients | RIRL/070922/ 1032 | RIRL/030822/ 1019 | RIRL/030822/ 1020 |
| Rivaroxaban | 1 | 2 | 4 |
| Microcrystalline Cellulose (MCC)/Carboxy Methyl Cellulose (CMC) Sodium | 12.0 | 12.0 | 12.0 |
| Sucralose | 2.0 | 2.0 | 2.0 |
| Xanthan Gum | 3.5 | 3.5 | 3.5 |
| Sodium Benzoate | 1.0 | 1.0 | 1.0 |
| Citric Acid anhydrous | 6.4 | 6.4 | 6.4 |
| Sodium citrate | 5.0 | 5.0 | 5.0 |
| Simethicone emulsion | 3.0 | 3.0 | 3.0 |
| Sodium Lauryl Sulfate | 1.0 | 1.0 | 1.0 |
| Frozen peppermint | 0.1 | 0.1 | 0.1 |
| Glycerin | 50.0 | 50.0 | 50.0 |
| Purified water | Q.S. to 1 mL | Q.S to 1 mL | Q.S to 1 mL |

Q.S.: Quantity Sufficient

Procedure:
a) The citric acid was added in purified water and mixed till gets completely solubilized;
b) The sodium citrate was added in solution of step (a) and mixed till gets completely solubilized;
c) The sodium benzoate was added in solution of step (b) and mixed till gets completely solubilized;
d) The sucralose was added in solution of step (c) and mixed till gets completely solubilized;
e) The simethicone was added in solution of step (d) till gets completely solubilized;
f) The Avicel-RC 591 was added in solution of step (e) and mixed till gets completely solubilized and till achieved desirable viscosity;
g) The sodium lauryl sulfate was added in solution of step (f) and mixed till gets completely solubilized;
h) The glycerin was added in solution of step (g) and mixed till gets completely solubilized;
i) The rivaroxaban was added in solution of step (h) and mixed till gets completely solubilized;
j) The xanthan gum was added in remaining quantity of glycerin in separate vessel and mixed till get homogenously dispersed;
k) The solution of step (h) was added into slurry of step (j) and continuously stirred the solution till get homogenously dispersed;
l) The flavoring agent was added in solution of step (k) and mixed it till gets completely dispersed;
m) The volume of step (l) was adjusted using purified water, mixed and homogenized the formulation using homogenizer till homogeneous formulation obtained.
n) The final formulation was stored in a HDPE bottle.

Example 4a: Thermal Stability Data of Batch No. RIRLU070922/1032

The thermal stability study was conducted for final formulation at accelerated stability condition 40° C.±2° C./NMT 75% RH and 25° C.±2° C./60±5% RH.

TABLE 6a

Results of stability study of batch No. RIRL/070922/1032

| Parameters TRF No. | Specification RIRLTRF | INITIAL 50008 | 40° C./NMT 25% RH | | | 25° C./60% RH | | |
|---|---|---|---|---|---|---|---|---|
| | | | 1 M 50034 | 3 M 50064 | 6 M 50099 | 3 M 50063 | 6 M 50098 | 9 M 50103 |
| Description | White to off white suspension | Complies | Complies | Complies | Complies | Complies | Complies | Complies |
| Assay of Rivaroxaban | 90%-110.0% of labelled amount | 100.7 | 101.9 | 101 | 101.7 | 100.9 | 101.5 | 101.7 |
| Assay of Sodium Benzoate | 90%-110.0% of labelled amount | 100.3 | 100.4 | 98.6 | 98.7 | 99.4 | 99.7 | 99.9 |
| pH | 3.4 to 4.5 | 3.99 | 3.93 | 3.81 | 3.91 | 3.81 | 3.92 | 3.95 |
| Zeta potential | −10 mV to −50 mV | (−17.1 mV) | (−15.1 mV) | (−16.4 mV) | (−18.0 mV) | (−15.5 mV) | (−13.5 mV) | (−14.5 mV) |
| Viscosity | 100 cP to 300 cP | 192.6 cP | 183.3 cP | 178.8 cP | 223.8 cP | 209.4 cP | 203.7 cP | 223.3 cP |
| Particle size | D(10): NMT 30 μm | 16.2 | 16.3 | 16.0 | 16.0 | 15.7 | 15.7 | 15.7 |
| | D(50): NMT 90 μm | 61.8 | 60.5 | 60.5 | 60.1 | 60.3 | 59.9 | 59.9 |
| | D(90): NMT 150 μm | 125.0 | 122.0 | 124.0 | 122.0 | 123.0 | 122.0 | 119.0 |
| Dissolution | NLT 80% in 15 min | 15 min: 96% (RSD: 2.6%) | NA | 15 min: 96% (RSD: 0.5%) | 15 min: 100% (RSD: 2.1%) | 15 min: 95% (RSD: 0.5%) | 15 min: 100% (RSD: 0.8%) | 15 min: 100% (RSD: 1.2%) |
| | | | | Related substances (By HPLC) | | | | |
| Single Max unknown | NMT 0.2% | ND | BQL | BQL | BQL | BQL | BQL | BQL |
| Total Impurities | NMT 1.0% | 0.00% | 0.00% | 0.00% | 0.00% | 0.00% | 0.00% | 0.00% |

NMT: Not More Than; NLT: Not Less Than; RH: Relative Humidity; M: Months; RSD: Relative Standard Deviation; BQL: Below Quantitation Limit; Single max unknown: Any single unknown impurity.

Example 4b: Thermal Stability Data of Batch No. RIRLU030822/1019     35

TABLE 6b

Results of stability study of batch No. RIRL/030822/1019

| Parameters TRF No. | Specification RIRLTRF | INITIAL RIRLTRF40008 | 40° C./NMT 25% RH | | |
|---|---|---|---|---|---|
| | | | 1 M RIRLTRF40011 | 3 M RIRLTRF40025 | 6 M RIRLTRF40029 |
| Description | White to off white suspension | Complies | Complies | Complies | Complies |
| Assay of Rivaroxaban | 90%-110.0% of labelled amount | 99.2 | 101 | 99.2 | 100 |
| Assay of Sodium Benzoate | 80%-110.0% of labelled amount | 100.4 | 100.2 | 98.2 | 97.4 |
| pH | 3.4 to 4.5 | 3.9 | 3.9 | 3.7 | 3.9 |
| Viscosity | 200 cps to 600 cps | 188.7 cP | 191.1 cP | 235.8 cP | 223.8 cP |
| Particle size | D(10): Between 5 μm to 30 μm | 13.4 | 13.3 | 12.5 | 13.1 |
| | D(50): Between 40 μm to 80 μm | 56.7 | 56.4 | 55.4 | 55.1 |
| | D(90): Between 100 μm to 150 μm | 120.0 | 120.0 | 119.0 | 116.0 |
| Dissolution | NLT 80% (Q) in 15 min | 15 min: 102% (RSD: 0.5%) | NA | 15 min: 96% (RSD: 1.1%) | 15 min: 98% (RSD: 1.1%) |
| | | | Related substances (By HPLC) | | |
| Open ring acid | NMT 0.2% | ND | BQL | BQL | BQL |
| Descarbonyl Impurity | NMT 0.2% | ND | BQL | ND | ND |

TABLE 6b-continued

| Results of stability study of batch No. RIRL/030822/1019 | | | | |
|---|---|---|---|---|
| Any unspecified degradation product | NMT 0.2% | ND | BQL | BQL | BQL |
| Total Impurities | NMT 0.5% | 0.00% | 0.00% | 0.00% | 0.00% |

| | | 25° C./60% RH | | |
|---|---|---|---|---|
| Parameters TRF No. | Specification RIRLTRF | 3 M RIRLTRF40024 | 6 M RIRLTRF40028 | 9 M RIRLTRF40031 + RIRLTRF40032 |
| Description | White to off white suspension | Complies | Complies | Complies |
| Assay of Rivaroxaban | 90%-110.0% of labelled amount | 98.3 | 100.4 | 100.7 |
| Assay of Sodium Benzoate | 80%-110.0% of labelled amount | 99.7 | 98.8 | 99.2 |
| pH | 3.4 to 4.5 | 3.8 | 3.9 | 3.9 |
| Viscosity | 200 cps to 600 cps | 218.4 cP | 223.8 cP | 218.1 cP |
| Particle size | D(10): Between 5 μm to 30 μm | 12.9 | 12.9 | 12.9 |
| | D(50): Between 40 μm to 80 μm | 56.4 | 55.4 | 55.3 |
| | D(90): Between 100 μm to 150 μm | 120.0 | 119.0 | 118.0 |
| Dissolution | NLT 80% (Q) in 15 min | 15 min: 95% (RSD: 0.7%) | 15 min: 100% (RSD: 0.5%) | 15 min: 98% (RSD: 0.5%) |
| Related substances (By HPLC) | | | | |
| Open ring acid | NMT 0.2% | BQL | BQL | BQL |
| Descarbonyl Impurity | NMT 0.2% | ND | ND | ND |
| Any unspecified degradation product | NMT 0.2% | BQL | BQL | BQL |
| Total Impurities | NMT 0.5% | 0.00% | 0.00% | 0.00% |

40

Example 4c: Thermal Stability Data of Batch No. RIRLU030822/1020

TABLE 6c

| Results of stability study of batch No. RIRL/030822/1020 | | | | |
|---|---|---|---|---|
| | | 40° C./NMT 25% RH | | |
| Parameters | Specification TRF No. | INITIAL RIRLTRF30015 | 1 M RIRLTRF30018 | 3 M RIRLTRF30024 | 6 M RIRLTRF30031 |
| Description | White to off white suspension | Complies | Complies | Complies | Complies |
| Assay of Rivaroxaban | 90%-110.0% of labelled amount | 98.9 | 100.9 | 99.4 | 99.4 |
| Assay of Sodium Benzoate | 80%-110.0% of labelled amount | 100.3 | 100.4 | 98.6 | 97.2 |
| pH | 3.4 to 4.5 | 3.9 | 3.9 | 3.8 | 3.9 |
| Viscosity | 200 cps to 600 cps | 193.2 cP | 184.5 cP | 196.2 cP | 192 cP |
| Particle size | D(10): Between 5 μm to 30 μm | 9.4 | 10.1 | 8.8 | 9.5 |
| | D(50): Between 40 μm to 80 μm | 57.3 | 60.8 | 57.8 | 58.5 |
| | D(90): Between 100 μm to 150 μm | 122.0 | 127.0 | 121.0 | 122.0 |

TABLE 6c-continued

| Results of stability study of batch No. RIRL/030822/1020 | | | | | |
|---|---|---|---|---|---|
| Dissolution | NLT 80% (Q) in 15 min | 15 min: 100% (RSD: 0.5%) | NA | 15 min: 94% (RSD: 3.1%) | 15 min: 97% (RSD: 0.5%) |
| Related substances (By HPLC) | | | | | |
| Open ring acid | NMT 0.2% | ND | BQL | BQL | BQL |
| Descarbonyl Impurity | NMT 0.2% | ND | BQL | BQL | ND |
| Any unspecified degradation product | NMT 0.2% | ND | BQL | BQL | BQL |
| Total Impurities | NMT 0.5% | 0.00% | 0.00% | 0.00% | 0.00% |

| | | | 25° C./60% RH | | |
|---|---|---|---|---|---|
| | Parameters | Specification | 3 M TRF No. RIRLTRF30023 | 6 M RIRLTRF30030 | 9 M RIRLTRF30034 |
| | Description | White to off white suspension | Complies | Complies | Complies |
| | Assay of Rivaroxaban | 90%-110.0% of labelled amount | 98.2 | 100.6 | 100.1 |
| | Assay of Sodium Benzoate | 80%-110.0% of labelled amount | 99.9 | 99.9 | 99.1 |
| | pH | 3.4 to 4.5 | 3.8 | 3.9 | 3.9 |
| | Viscosity | 200 cps to 600 cps | 214.8 cP | 214.8 cP | 212.4 cP |
| | Particle size | D(10): Between 5 μm to 30 μm | 9.3 | 12.9 | 9.8 |
| | | D(50): Between 40 μm to 80 μm | 58.9 | 55.4 | 59.5 |
| | | D(90): Between 100 μm to 150 μm | 124.0 | 119.0 | 125.0 |
| | Dissolution | NLT 80% (Q) in 15 min | 15 min: 96% (RSD: 1.1%) | 15 min: 98% (RSD:0.9%) | 15 min: 97% (RSD:0.5%) |
| | Related substances (By HPLC) | | | | |
| | Open ring acid | NMT 0.2% | BQL | BQL | BQL |
| | Descarbonyl Impurity | NMT 0.2% | ND | ND | ND |
| | Any unspecified degradation product | NMT 0.2% | BQL | BQL | BQL |
| | Total Impurities | NMT 0.5% | 0.00% | 0.00% | 0.00% |

Based on all above stability data, it is concluded that rivaroxaban oral suspension is stable at accelerated condition up to 6 months and at room temperature (25° C.±2° C.) up to 9 months.

Particle Size: Particle size was measured by using Malvern Mastersizer 3000 instrument.

Sample Preparation: Accurately transfer about 4 gm sample into 50 ml beaker, added 20 ml water and mix well, sonicate it for 30 seconds.

Dispersant: Water

Note: Avoid bubbles during sample preparation.

Procedure:

Wash dispersant tank first with water and with methanol followed by twice wash with water and finally fill dispersant tank with dispersant. Set method parameters as mentioned above. Initialize instrument and measure background. Once initialization and background finished, add sample preparation with continuous stirring to dispersant tank and observe obscuration. If obscuration found stable and within the specified range then start sample measurement. Report average result of three measurements.

After completion of analysis wash dispersant tank with water once, followed by wash with methanol twice. In between the sample analysis wash dispersant tank once with methanol and following wash with dispersant.

Zeta Potential: Zeta potential was measured by using Malvern Zetasizer ZEN3600 instrument.

Sample preparation: Transfer 3 ml of sample suspension in to 10 ml volumetric flask and dilute up to mark with water (Milli-Q) and mix well.

Precaution: Sample to be analyze immediately or else otherwise sedimentation of sample will be seen and due to that variation result will be occur.

Procedure:

Note: The cuvettes should be filled to a depth of between 6 mm to 8 mm.

Fill the sample in to cuvettes, then insert dip cell with cuvette in to sample holder and start to measure sample. Avoid bubbles in sample preparation while filling dip cell. Thoroughly rinse dip cell with pure dispersant before next sample analysis.

Viscosity: Viscosity was measured by using Brookfield viscometer.

Procedure: Set the instrument as per the requirement, add sample in the beaker/suitable container and maintain the temperature 25±2° C. Select the spindle and run the instrument at 50 rpm. Record results.

Example 5: Stress Studies

Stress studies (photostability and freeze-thaw) were performed to evaluate and verify the final product processing and handing during the storage and transportation to establish controlled storage and handling.

5.1: Photostability Studies

The final formulation was filled into the 185 mL HDPE bottle subjected to a photo stability study. The total light exposure of an overall illumination of 1.2 million lux hours and an integrated near ultraviolet energy of not less than 200-watt hours/square meter was provided.

TABLE 7

| | | | Results of photostability study | | | |
|---|---|---|---|---|---|---|
| | | | | TYPE OF PACKAGING | | |
| | Condition Time Point TRF No. | Specification RIRTRF | Primary pack 50049 | Secondary pack 50050 | Aluminum Wrapped bottle 50051 | Clear PET Bottle 50052 |
| 1 | Description | White to off white suspension | Off White Suspension | Off White Suspension | Off White Suspension | Off White Suspension |
| 2 | Assay of Rivaroxaban | 90.0% to 110.0% of labelled amount | 99.8 | 100.3 | 99.6 | 99.6 |
| 3 | Assay of Sodium Benzoate | 80% to 110.0% of labelled amount | 98.8 | 99.1 | 98.7 | 98.7 |
| 4 | pH | 3.5-4.5 | 3.9 | 3.9 | 3.9 | 3.9 |
| 5 | | Related substances (By HPLC) | | | | |
| | Single Max unknown impurity | NMT 0.2% | BQL | BQL | BQL | BQL |
| | Total Impurities | NMT 0.5% | 0.00% | 0.00% | 0.00% | 0.00% |

BQL: Below Quantification Limit; NMT: Not More Than; Single max unknown impurity: Any single unknown impurity.

As per the results, when product was exposed to light filled in different bottles, there was no increase in impurities or decrease in assay of rivaroxaban and preservative observed, which suggest that product is not getting affected by exposure to light.

5.2: Freeze Thaw Studies

The final formulation bottles were subjected to a temperature cycle of −20° C.±5° C. for 2 days followed by 40° C.±2° C. for 2 days. The product bottles were subjected to three such cycles.

TABLE 8

| | | | Results of freeze thaw study | |
|---|---|---|---|---|
| | | | Condition | |
| | | | INITIAL | FREEZE THAW Time Point 3$^{RD}$ CYCLE |
| | | | TRF No. | |
| | | Specification | RIRLTRF50044 | RIRLTRF50048 |
| 1 | Description | White to off white suspension | Off White Suspension | White Suspension |
| 2 | Assay of Rivaroxaban | 90.0% to 110.0% of labelled amount | 99.9 | 99.9 |
| 3 | Assay of Sodium Benzoate | 80% to 110.0% of labelled amount | 94.5 | 94.9 |

TABLE 8-continued

| | | | Results of freeze thaw study | |
|---|---|---|---|---|
| | | | Condition | |
| | | | INITIAL | FREEZE THAW Time Point 3$^{RD}$ CYCLE |
| | | | TRF No. | |
| | | Specification | RIRLTRF50044 | RIRLTRF50048 |
| 4 | pH | 3.5-4.5 | 3.9 | 3.9 |
| 5 | | Related substances (By HPLC) | | |

TABLE 8-continued

| | | | Results of freeze thaw study | |
|---|---|---|---|---|
| | | | Condition | |
| | | | INITIAL | FREEZE THAW Time Point 3$^{RD}$ CYCLE |
| | | | TRF No. | |
| | | Specification | RIRLTRF50044 | RIRLTRF50048 |
| | Single Max unknown impurities | NMT 0.2% | BQL | BQL |
| | Total Impurities | NMT 0.5% | 0.00% | 0.06% |

BQL: Below Quantification Limit; NMT: Not More Than; Single max unknown: Any single unknown impurity.

The results indicated that the product stability was not affected by the extreme temperature conditions encountered by the drug product and the product can withstand limited temperature excursions during the transportation process.

Example 6: Comparative Study of Rivaroxaban Marketed Tablet and Liquid Formulation-Dissolution

TABLE 9

Result of dissolution study of Xarelto ® tablet
Xarelto ® 20 mg tablet (Batch No. BT15RA1)

| USP app. - II (Paddle) | | Volume - 900 ml | Speed - 75 rpm |
| --- | --- | --- | --- |
| | | % Drug Release | |
| Time point (min) | 0.1N HCl + 0.4% SLS | 0.01N HCl + 0.4% SLS | pH 6.8 Phosphate Buffer + 0.4% SLS | Water + 0.4% SLS |
| 10 min | 69 | 75 | 81 | 80 |
| 15 min | 77 | 85 | 89 | 91 |
| 20 min | 81 | 88 | 92 | 93 |
| 30 min | 86 | 92 | 95 | 95 |
| 45 min | 89 | 94 | 96 | 96 |
| 60 min(Rec) | 92 | 95 | 97 | 96 |

TABLE 10

Result of dissolution study of rivaroxaban (1 mg/mL) oral suspension
RIVAROXABAN ORAL SUSPENSION 1 MG/ML

| USP app. - II (Paddle) | | Volume - 900 ml | Speed - 75 rpm |
| --- | --- | --- | --- |
| | | % Drug Release | |
| Time point (min) | 0.1N HCl | pH 4.5 Acetate buffer | pH 6.8 Phosphate Buffer | Water |
| 10 min | 88 | 83 | 90 | 95 |
| 15 min | 93 | 96 | 97 | 96 |
| 20 min | 99 | 98 | 100 | 101 |
| 30 min | 102 | 104 | 102 | 102 |
| 45 min | 102 | 105 | 103 | 102 |
| 60 min(Rec) | 104 | 105 | 103 | 103 |

The results of comparative dissolution study of rivaroxaban marketed tablet and liquid formulation proved that the rivaroxaban liquid formulation gives higher dissolution compare to marketed tablet formulation.

The invention claimed is:

1. An oral liquid formulation, comprising:
rivaroxaban in a concentration of from about 1 mg/mL to about 10 mg/mL;
one or more viscosifying agents comprising a combination of microcrystalline cellulose and carboxymethylcellulose sodium, xanthan gum, or a combination thereof in a concentration of from about 1 mg/mL to about 16 mg/ml;
one or more buffering agents in a concentration of from about 4 mg/mL to about 20 mg/mL;
a wetting agent selected from the group consisting of sodium lauryl sulfate, sodium tetradecyl sulfate, dodecyl sulfate, lauryl glucoside or a combination thereof;
an anti-foaming agent;
one or more pharmaceutically acceptable excipients; and
a vehicle comprising water and glycerin,
wherein the glycerin is present in a concentration of from about 30 mg/mL to about 100 mg/ml;
wherein the oral liquid formulation is in the form of a ready to use suspension;
wherein the oral liquid formulation has a pH of from about 3.5 to about 4.5; and wherein the oral liquid formulation has less than 0.5% rivaroxaban related substance impurities after storage at 25° C.±2° C./60±5% RH up to 9 months.

2. The oral liquid formulation of claim 1, wherein the rivaroxaban is present in a concentration of about 2 mg/mL.

3. The oral liquid formulation of claim 1, wherein the rivaroxaban is present in a concentration of about 4 mg/mL.

4. The oral liquid formulation of claim 1, wherein the one or more viscosifying agents comprises a combination of microcrystalline cellulose and carboxymethylcellulose sodium, xanthan gum, or a combination thereof in a concentration of from about 1 mg/mL to about 16 mg/mL.

5. The oral liquid formulation of claim 1, wherein the one or more viscosifying agents comprises a combination of microcrystalline cellulose and carboxymethylcellulose sodium in a concentration of from about 5 mg/mL to about 15 mg/mL.

6. The oral liquid formulation of claim 1, wherein the one or more viscosifying agents comprises a combination of microcrystalline cellulose and carboxymethylcellulose sodium in a concentration of about 12 mg/mL.

7. The oral liquid formulation of claim 1, wherein the combination of microcrystalline cellulose and carboxymethylcellulose sodium comprises about 82% to about 89% of microcrystalline cellulose and about 11% to about 18% of carboxymethylcellulose sodium.

8. The oral liquid formulation of claim 1, wherein the one or more viscosifying agents comprises a xanthan gum in a concentration of from about 1 mg/mL to about 5 mg/mL.

9. The oral liquid formulation of claim 1, wherein the one or more viscosifying agents comprises a xanthan gum in a concentration of about 3.5 mg/mL.

10. The oral liquid formulation of claim 1, wherein the anti-foaming agent is present in a concentration of from about 0.5 mg/mL to about 20 mg/mL.

11. The oral liquid formulation of claim 1, wherein the anti-foaming agent comprise a simethicone.

12. The oral liquid formulation of claim 1, wherein the anti-foaming agent comprise a 30% simethicone emulsion.

13. The oral liquid formulation of claim 1, wherein the one or more buffering agents in a concentration of from about 8 mg/mL to about 20 mg/mL.

14. The oral liquid formulation of claim 1, wherein the one or more buffering agents comprises sodium citrate, citric acid, or a combination thereof.

15. The oral liquid formulation of claim 1, wherein the wetting agent is present in a concentration of from about 0.5 mg/mL to about 10 mg/mL.

16. The oral liquid formulation of claim 1, wherein the wetting agent is present in a concentration of from about 0.5 mg/mL to about 5 mg/mL.

17. The oral liquid formulation of claim 1, wherein the wetting agent comprises sodium lauryl sulfate in a concentration of from about 0.5 mg/mL to about 5 mg/mL.

18. The oral liquid formulation of claim 1, wherein the one or more pharmaceutically acceptable excipients comprises a sweetening agent selected from the group consisting of sucralose, trehalose, xylose, dextrose, tagatose, glycerol, dulcitol, lactitol, saccharine or the corresponding sodium, potassium or calcium salt, cyclamate or the corresponding sodium or calcium salt, aspartame, or acesulfame or the potassium salt thereof, ammonium glycyrrhizinate, alitame, inulin, isomalt, neohesperidin dihydrochalcone, thaumatin or a combination thereof.

19. The oral liquid formulation of claim 1, wherein the one or more pharmaceutically acceptable excipients comprises a sweetening agent in a concentration of from about 0.1 mg/mL to about 10 mg/mL.

20. The oral liquid formulation of claim 1, wherein the one or more pharmaceutically acceptable excipients comprises a preservative selected from the group consisting of benzoic acid, potassium sorbate, sodium benzoate, chlorobutanol, benzalkonium chloride, benzethonium chloride, benzyl alcohol, chlorobutanol, m-cresol, myristyl gamma picolinium chloride, phenol, 2-phenoxyethanol, phenyl mercuric nitrate, phenyl ethyl alcohol or a combination thereof.

21. The oral liquid formulation of claim 1, wherein the one or more pharmaceutically acceptable excipients comprises a preservative in a concentration of from about 0.01 mg/mL to about 10 mg/mL.

22. The oral liquid formulation of claim 1, wherein the one or more pharmaceutically acceptable excipients comprises a flavoring agent selected from the group consisting of vanilla, citrus oil, including lemon, orange, grape, lime and grapefruit, and fruit essences, including apple, banana, pear, peach, strawberry, raspberry, cherry, plums pineapple, apricot, peppermint, frozen peppermint, tutti frutti flavor or a combination thereof.

23. The oral liquid formulation of claim 1, wherein the one or more pharmaceutically acceptable excipients comprises a flavoring agent in a concentration of from about 0.01 mg/mL to about 1 mg/mL.

24. The oral liquid formulation of claim 1, wherein the oral liquid formulation has a viscosity of about 200 cP to about 600 cP and rivaroxaban D90 particle size between about 100 microns to about 150 microns.

\* \* \* \* \*